United States Patent [19]

Tabata et al.

[11] Patent Number: 4,513,753
[45] Date of Patent: Apr. 30, 1985

[54] HEARTBEAT RATE INDICATOR

[75] Inventors: Junichi Tabata; Masahiro Torii; Hiroshi Oikawa; Minoru Sawada; Yasuyuki Masui, all of Tokyo, Japan

[73] Assignee: Kabushiki Kaisha Daini Seikosha, Tokyo, Japan

[21] Appl. No.: 439,324

[22] Filed: Nov. 4, 1982

[30] Foreign Application Priority Data

Nov. 17, 1981 [JP] Japan ............................. 56-184247

[51] Int. Cl.³ ............................................. A61B 5/02
[52] U.S. Cl. .................................... 128/706; 128/710
[58] Field of Search ............... 128/703, 639, 706, 708, 128/709, 710, 696, 698, 690

[56] References Cited

U.S. PATENT DOCUMENTS

| 4,027,663 | 6/1977 | Fischler et al. | 128/710 |
| 4,120,294 | 10/1978 | Wolfe | 128/710 |
| 4,230,127 | 10/1980 | Larson | 128/706 |
| 4,312,358 | 1/1982 | Barney | 128/706 |
| 4,350,164 | 9/1982 | Allain, Jr. | 128/696 |

Primary Examiner—Lee S. Cohen
Assistant Examiner—Steven Falk
Attorney, Agent, or Firm—Robert E. Burns; Emmanuel J. Lobato; Bruce L. Adams

[57] ABSTRACT

A heartbeat rate indicator has a detection electrode on the surface of the housing such as a wristwatch case and the element of a circuit-input portion in which the existence of a switch connected to the detection electrode prevents the element from destroying with electrostatic charge produced at the moment of touching the detection electrode with the human body, the clothes or the like.

Because in the non-depression state of the detection electrode, the detection electrode is connected elastically through the switch to one terminal of a power source so that the electrostatic charge produced at the moment of touching the detection electrode with the human body discharges to the one terminal of the power source.

9 Claims, 5 Drawing Figures

HEARTBEAT RATE INDICATOR

BACKGROUND OF THE INVENTION

This invention relates to a heartbeat rate indicator and more particularly to the construction of a heartbeat rate indicator in which a heartbeat rate measuring circuit is prevented from electrostatic destruction.

Conventionally, there is used electrocardiography as one method of heartbeat rate measure. This method detects a small electric signal of the heart produced in the human body prior to the contraction of the heart.

The features of this method are:

(1) to measure the heartbeat rate by touching two metal-electrodes with two human limbs, and with high reliability, and (2) to be adapted to a small size- and long life-device because the detection of the electric heart signal is made with low power dissipation.

A small and portable heartbeat rate indicator is made by use of electrocardiography. However, in the conventional circuit and electrode-construction, the input portion of the circuit is susceptible of being destroyed by electrostatic charge at the moment of touching a detection electrode with the human body, the clothes or the like. As a result, the function of heartbeat rate-detection and measuring is deteriorated.

SUMMARY OF THE INVENTION

An object of this invention is to provide a heartbeat rate indicator for eliminating the conventional defects and to provide a heartbeat rate indicator having high reliability and in which the breakdown of heartbeat rate detection and measurement due to electrostatic charge are prevented, irrespective of the location of the heartbeat rate indicator.

Another object of this invention is to provide a heartbeat rate indicator having a detection electrode and a switch which can be opened with depression of the detection electrode, wherein one terminal of the switch is connected to the detection electrode and another terminal of the switch is connected to one terminal of a power source.

DESCRIPTION OF THE PREFERRED EMBODIMENT

Figure 1:
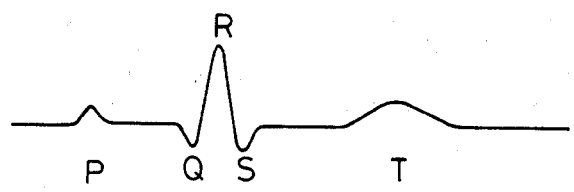
FIG. 1 is a signal-wave of a representative cardiogram.

FIG. 1 is a signal-wave such as obtained by a cardiograph. Generally, the cardio-electric potential signal induced between the right limb of the human body and the left limb thereof is composed of P wave, Q-R-S wave and T wave and these waves appear periodically. The amplitude of the Q-R-S wave is the greatest among these waves and ranges from about 0.2 mV to 1.0 mV although the difference of the amplitude exists among persons. Accordingly, the method for detecting the Q-R-S wave is generally employed.

Further, the noise of commercial frequency induced on the surface of the human body is superposed.

In the heartbeat rate measurement, it is required to eliminate the commercial frequency noise of great amplitude and to pick up the cardio-electric potential signal of small amplitude.

Figure 2:
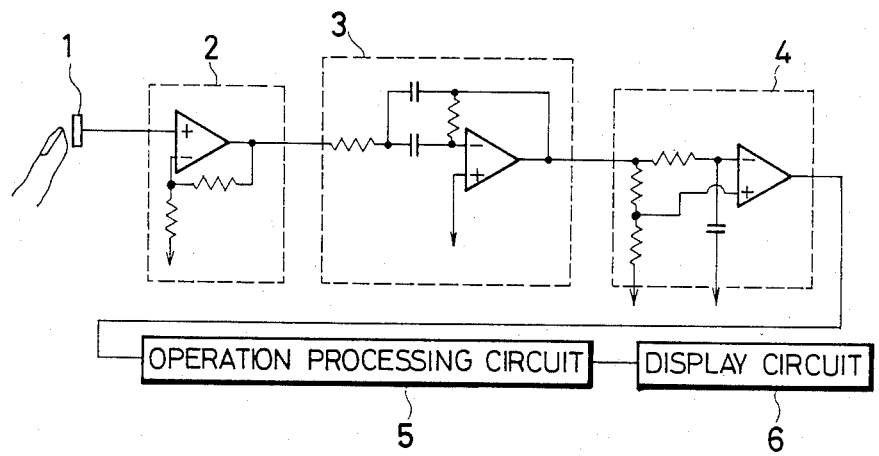
FIG. 2 is an embodiment of a detection circuit.

One embodiment of the detection circuit using electrocardiography is shown in FIG. 2.

Numeral 1 is a detection electrode composed of an electro-conductor such as a stainless steel or a silver chloride. The detection electrode 1 is conveniently exposed on the surface of the housing of the heartbeat rate indicator.

When a person desires to measure his heartbeat rate, his body surface, for example, a portion of the skin of one hand (right hand) contacts with the circuit ground and a portion of the skin of the other hand (left hand), for example, a fingertip, contacts with the detection electrode. This operation of the heartbeat measurement is executed readily by the connection between circuit ground and the caseback. The detection electrode 1 is connected to an amplifier 2. The amplifier 2 is selected to have an arbitrary amplification rate by means of an operational amplifier and a plurality of resistors. The cardio-electric potential signal and noise are amplified to a predetermined amplitude and input to a band pass filter 3. The band pass filter 3 is composed of an operational amplifier, a plurality of resistors and a plurality of capacitors and both the central frequency of the band pass filter and the quality factor Q are selected arbitrarily. The commercial frequency noise is eliminated by the band pass filter 3 so that the cardio-electric potential is output from the band pass filter 3. The output of the band pass filter 3 is input to a voltage comparator 4. The voltage comparator 4 detects only the cardio-electric potential and produces a pulse signal at the output terminal. The output signal of the voltage comparator 4 is input to an operation processing circuit 5. The period (Tsec) of the circuit pulse signal is counted and the heartbeat number per one minute is arithmetically determined by the operation processing circuit 5.

The relationship between the period (Tsec) of the input pulse and the heartbeat number is represented by the following equation:

$$p = 60(\text{sec})/T$$

The output signal of the operation processing circuit 5 is input to a display circuit 6 and drives the liquid crystal display element so that the heartbeat rate is indicated.

The cardio-electric potential system may save energy by including a switching circuit for controlling the energy supply from the power source. Namely the switching input is positioned in the OFF state when the heartbeat rate is not measured. However, the input transistor of the operational amplifier which comprises the amplifier 2 is destroyed electrostatically when the detection electrode 1 on the surface of the heartbeat rate indicator receives the electrostatic charge.

The generation of electrostatic charge occurs readily in daily life, such as by a person putting on or taking off clothes. The electrostatic electricity is discharged when the charged human body approaches near to the detection electrode 1.

According to this invention, the electrostatic destruction of the detection circuitry is prevented by the method and construction described hereinafter.

Figure 3:
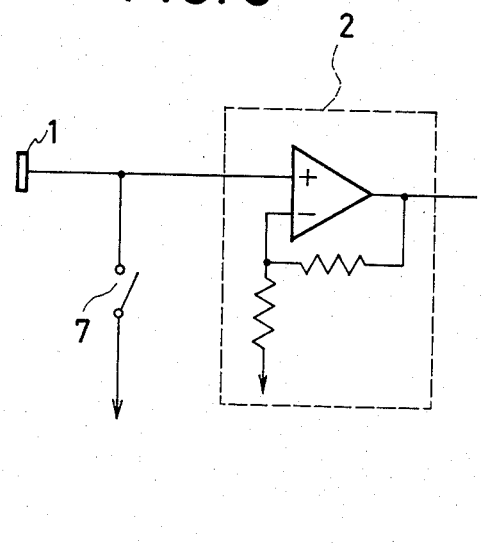
FIG. 3 is an explanatory diagram for understanding the electrical operation of the heartbeat rate indicator according to this invention.

The principle of this invention will be described with reference to FIG. 3 of the drawing.

To prevent unnecessary complication of the figure, only the input portion of the detection circuit is shown in the drawing.

(1) In the normal state (in the case of not using the heartbeat rate indicator), the detection electrode 1 is grounded through a switch 7. Accordingly, the electrostatic charge flows to the ground level in the event it discharges to the detection electrode 1.

(2) In the case of measuring the heartbeat rate, a person first brings his fingertip into contact with the detection electrode. At this moment, the electrostatic charge charged on the surface of his body flows to the ground level through the switch 7.

Then the detection circuit initiates operation when the switch 7 is changed to the OFF position.

FIG. 4 shows the construction of a heartbeat rate indicator having the detection electrode of this invention for realizing the prevention of the electrostatic disruption.

Figure 4A:
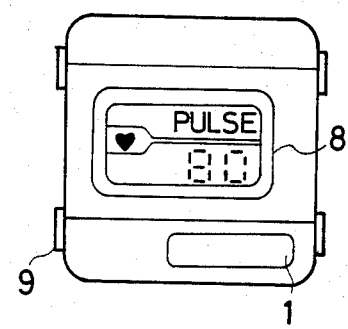
FIG. 4A is a plan view of a heartbeat rate indicator according to this invention.

FIG. 4A shows a plan view of a heartbeat rate indicator. The number of heartbeats is displayed on a display 8. In the case of execution of the heartbeat rate measurement, the heartbeat rate indicator can measure heartbeat rate when the measurement mode switch 9 is in the ON state, becasue the voltage of the power source is applied to the heartbeat rate measuring circuit. In this state, a person brings his fingertip into contact with the detection electrode 1.

Figure 4B:
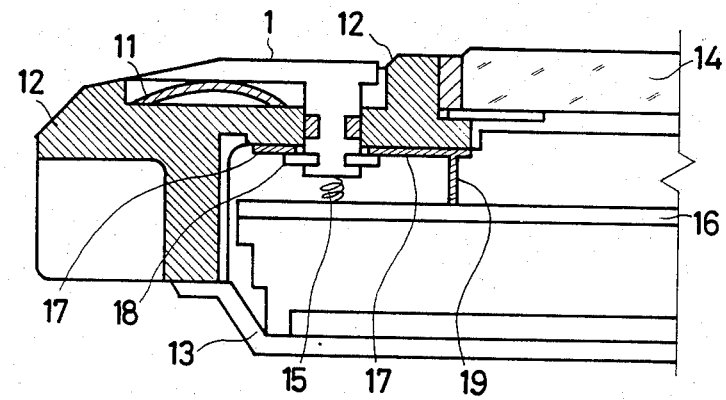
FIG. 4B is a sectional view of the heartbeat rate indicator according to this invention.

FIG. 4B shows a cross-sectional view of the detection electrode construction. The depressible detection electrode 1 is monably supported through a spring 11 with a side cover 12. The side cover 12 is formed of an insulator such as plastic and the detection electrode 1 is separated from a caseback 13 with the side cover 12. The caseback 13 is made of stainless steel. Reference numeral 14 is a front glass. One terminal of the detection electrode 1 is connected through a lead terminal 15 to the input lead on a circuit board 16. The lead terminal 15 is formed spirally to exhibit a spring characteristic.

A ring 18 for fixing is made from a conductive material and is inserted in a recess of the detection electrode 1. A lead member 17 is attached to one portion of the inner wall surface of the detection electrode and the lead member 17 is made from conductive material.

One portion of the lead member 17 contacts the ring 18 and does not contact directly with the detection electrode 1. The other portion of the lead member 17 is connected through a lead terminal 19 to the ground lead on the circuit board 16. By such a construction, the lead member 17 comprises a stationary switch contact portion, and the ring 18 comprises a movable switch contact portion which moves into and out of electrical contact with the stationary switch contact portion in dependence on the position of the depressible detection electrode 1.

The lead terminal 19 may be connected directly to the ground potential instead of being connected to ground through the circuit board. The depressible detection electrode 1 constructed as mentioned above is biased or urged upward by the spring 11 in the normal state so that the ring 18 contacts with the lead member 17.

At this time the detection electrode 1 is connected electrically through the lead member 17 and the lead terminal 19 to the ground potential. This corresponds to the state that the switch 7 is on the closed and in state. Accordingly, the electrostatic electricity flows to the ground level in by-pass relationship with respect to the circuits 2, 3, 4, 5 and 6, even if an electrostatic discharge is produced by, for example, touching of the clothes to the detection electrode 1.

In case of measurement of the heartbeat rate, the electrostatic charge charged and accumulated on the human body flows through a conductive discharge path 1, 18, 17, 19, 16 to the ground level at the moment that a person contacts the detection electrode 1.

Next, the person depresses the detection electrode 1 slightly. At this time the ring 18 is disengaged from the lead member 17 so that the detection electrode 1 is electrically disconnected from the ground level. This corresponds to the state that the switch 7 is open and in the OFF position as shown in FIG. 3 so that measurement of the heartbeat rate starts.

Finally, when the fingertip of the person is removed from the detection electrode 1 after the measurement of the heartbeat rate, the detection electrode 1 is restored to the normal position by the restoring force of the spring 11 so that it is grounded electrically. As a result to the electrostatic destruction of the detection circuit is prevented.

According to the heartbeat indicator having the detection electrode construction of this invention, (1) in the normal state (in the case of not using the heartbeat rate indicator), the detection circuit is securely protected against the discharge of electrostatic charge produced incidentally because the detection electrode is grounded electrically.

(2) in the case of measuring the heartbeat rate, the electrostatic charge charged and stored on the surface of the human body flows to the ground level at the moment that a portion of a person's skin contacts with the detection electrode 1.

The detection circuit is protected securely from the electrostatic charge discharged at the initial time of the measurement because the measurement of the heartbeat rate does not commence until depression of the detection electrode.

Accordingly, this invention can provide a small-size and long-life heartbeat rate indicator having the above mentioned features and high reliability.

What is claimed is:

1. A heartbeat rate indicator comprising: a depressible detection electrode; an amplifier connected to receive and amplify a signal from said detection electrode; a filter connected to said amplifier for passing part of the amplified signal output from said amplifier; an operation processing circuit connected to receive the filtered output signal from said filter for determining a heartbeat number; display means for indicating the heartbeat number; and switch means having a normally closed state for electrically connecting said detection electrode and one voltage potential of a power source to effect grounding of the detection electrode and being switchable to an open state upon depression of said detection electrode to effect measurement of the heartbeat.

2. A heartbeat rate indicator as claimed in claim 1; wherein said detection electrode is connected elastically through said switch means to said one voltage potential of said power source when in the nondepressed state and electrically connected to said amplifier when in the depressed state.

3. A heartbeat rate indicator comprising: a depressible detection electrode for detecting a cardio-electric potential signal; circuit means having an operation processing means for determining a heartbeat number from the detected signal and display means for indicating said heartbeat number; an electrically insulating member; a lead member disposed on the surface of said insulating member and connected to one voltage potential of a power source; a contact portion connected electrically to said detection electrode and being movable therewith; and elastic means connected to said circuit means for electrically connecting said contact portion to said lead member when said detection electrode is not depressed to effect grounding of the detection electrode and for electrically disconnecting said contact portion from said lead member when said detection electrode is depressed to effect measurement of the heartbeat.

4. A heartbeat rate indicator for measuring and displaying the heartbeat rate of a person comprising: a detection electrode for detecting cardio-electric potential signals indicative of heartbeat rate from the skin surface of a person during use of the heartbeat rate indicator; circuit means receptive of the cardio-electric potential signals for determining therefrom the heartbeat rate and for displaying information corresponding to the determined heartbeat rate; and means coacting with the detection electrode for effecting the discharge of electrostatic charge accumulated on the person's body prior to detection of the cardio-electric potential signals, the means coacting with the detection electrode comprising means for flowing the accumulated electrostatic charge in by-pass relationship with respect to the circuit means.

5. A heartbeat rate indicator according to claim 4; wherein the means coacting with the detection electrode for effecting the discharge of accumulated electrostatic charge comprises means mounting the detection electrode for movement between first and second positions, biasing means for biasing the detection electrode to the first position, and means defining a conductive discharge path electrically connectable to the detection electrode when the same is in the first position for effecting the flow of accumulated electrostatic charge in by-pass relationship with respect to the circuit means and electrically disconnectable from the detection electrode when the same is in the second position.

6. A heartbeat rate indicator according to claim 5; wherein the means defining a conductive discharge path includes switch means having a first switching state for electrically connecting the detection electrode to the conductive discharge path and a second switching state for electrically disconnecting the detection electrode from the conductive discharge path.

7. A heartbeat rate indicator according to claim 6; wherein the switch means comprises a stationary contact portion electrically connected to the conductive discharge path, and a movable contact portion affixed to the movable detection electrode for movement therewith and positioned to make electrical contact with the stationary contact portion when the detection electrode is in the first position and to not make electrical contact with the stationary contact portion when the detection electrode is in the second position.

8. A heartbeat rate indicator according to claim 5; wherein the means mounting the detection electrode comprises means mounting the detection electrode for inward movement from the first position to the second position in response to depression thereof by the person.

9. A heartbeat rate indicator according to claim 4; further including a casing configured to be worn on the wrist of the person and containing therein the circuit means; and wherein the means coacting with the detection electrode for effecting the discharge of accumulated electrostatic charge comprises means mounting the detection electrode on the casing for movement between first and second positions, biasing means for biasing the detection electrode to the first position, and means defining a conductive discharge path electrically connectable to the detection electrode when the same is in the first position for effecting the flow of accumulated electrostatic charge in by-pass relationship with respect to the circuit means and electrically disconnectable from the detection electrode when the same is in the second position.

* * * * *